United States Patent [19]

Umemura et al.

[11] 4,256,914
[45] Mar. 17, 1981

[54] CATALYTIC OXIDATION OF METHACROLEIN

[75] Inventors: Sumio Umemura; Kyoji Ohdan; Fumihiko Sakai; Kenichi Suzuki; Toshihiko Hogami; Masataka Fuginaga, all of Ube, Japan

[73] Assignee: Ube Industries, Ltd., Ube, Japan

[21] Appl. No.: 68,198

[22] Filed: Aug. 17, 1979

[30] Foreign Application Priority Data

Aug. 25, 1978 [JP] Japan ............................ 53-102748

[51] Int. Cl.$^3$ ................... C07C 51/25; C07C 57/055
[52] U.S. Cl. ................................... 562/535; 252/435; 252/437
[58] Field of Search ................. 562/535; 252/435, 437

[56] References Cited

U.S. PATENT DOCUMENTS

| 3,875,220 | 4/1975 | White et al. | 562/535 |
| 4,017,423 | 4/1977 | White et al. | 562/535 |

FOREIGN PATENT DOCUMENTS 2514232  10/1975  Fed. Rep. of Germany ........... 562/535

Primary Examiner—Vivian Garner
Attorney, Agent, or Firm—Haseltine and Lake

[57] ABSTRACT

Methacrolein is catalytically oxidized into methacrylic acid in the vapor phase at a temperature of 200° to 450° C. The catalyst used is comprised of molybdenum, phosphorus, potassium and/or cesium, vanadium, silver and/or tellurium, and oxygen, and represented by the formula:

$$Mo_{12}P_aA_bV_cX_dO_e$$

wherein A is K and/or Cs and X is Ag and/or Te, and $a=0.5-5$, $b=0.1-4$, $c=0.05-3$, $d=0.001-2$ and e is a positive number required by the valence states of the other elements present.

11 Claims, No Drawings

CATALYTIC OXIDATION OF METHACROLEIN

BACKGROUND OF THE INVENTION (1) Field of the Invention

This invention relates to a process for catalytically oxidizing methacrolein in the vapor phase with molecular oxygen to produce methacrylic acid, wherein an improved catalyst is used giving an enhanced yield of methacrylic acid and exhibiting a long catalyst life.

(2) Description of the Prior Art

Many catalysts have been heretofore proposed which are used for oxidizing unsaturated aldehydes, such as acrolein and methacrolein at an elevated temperature in the vapor phase with molecular oxygen to produce corresponding unsaturated carboxylic acids, such as acrylic acid and methacrylic acid. However, proposals of the catalysts used for the oxidation of methacrolein to methacrylic acid are fewer in number than those of the catalysts used for the oxidation of acrolein to acrylic acid.

Certain catalysts were proposed as being capable of being used both for the oxidation of acrolein and the oxidation of methacrolein. It is generally accepted, however, that such catalysts exhibit reduced catalytic activity for the oxidation of methacrolein to methacrylic acid as compared with catalytic activity for the oxidation of acrolein to acrylic acid. That is, the yield of methacrylic acid is far lower than the yield of acrylic acid, provided that the same catalyst is used in the respective oxidation reactions. It is presumed that one of the reasons for which the yield of methacrylic acid is lower than the yield of acrylic acid is that methacrolein has a branched carbon chain, i.e., a methyl group, which is susceptible to oxidation, and thus, it is difficult to selectively oxidize the aldehyde group without the oxidation of the methyl group.

Heretofore, proposed catalysts used for the oxidation of methacrolein to methacrylic acid have some of the following defects: (1) the conversion of methacrolein, the selectivity to methacrylic acid and the yield of methacrylic acid are low; (2) the reaction temperature is undesirably high which influences the utility and the life of the catalyst and further causes side reactions; and, (3) the durability is poor. Typical examples of conventional catalysts for use in the oxidation of methacrolein are those which contain, as the essential elements, molybdenum, phosphorus, vanadium and an alkali metal. Illustrations of such catalysts are enumerated, for example, as in the following catalyst compositions: Mo-P-V-X-O (X=at least one metal of K, Rb, Cs and Tl; Japanese Laid-open patent application No. 82,013/1975), Mo-P-V-X-Y-O (X=at least one metal of K, Rb, Cs and Tl, Y=at least one metal of Sr, Zn, Cd, Nb, B, Pb, Bi and W; Japanese Laid-open patent application No. 123,619/1975 corresponding to U.S. Pat. No. 4,075,244), Mo-P-Cs-X-O (X=at least one metal of V, Nb and Tl; Japanese Laid-open patent application No. 135,020/1975), Mo-P-X-Y-O (X=at least one metal of V, Nb and Ta, Y=at least one metal of K and Tl; Japanese Laid-open patent application No. 65,713/1976); P-Mo-X-Y-O (X=at least one metal of K, Rb, Cs and Tl, Y=at least one metal of V, Fe, Mn, Ni, Ta, W, Sb, Co, Nb, Zn, Cd, U, Bi and Sn; Japanese Laid-open patent application No. 115,413/1976); Mo-P-X-Y-O (X is at least one metal of V, Fe, Pb and Ni, Y=at least one metal of K, Rb, Cs and Tl; Japanese Laid-open patent application No. 52,120/1976); and Mo-P-X-Y-O (X=at least one metal of K, Cs, Rb and Tl, Y=at least one metal of Ni, Sn, V, W, In, Zr and Ba; Japanese Laid-open patent application No. 57,117/1977).

Furthermore, a catalyst having the composition of Mo-V-P-O, which may optionally contain at least one metal of Bi, As, B, Ce, Cr, Ag, Fe, W, Pb, Mn, Tl, Te, Ni, Nb, B, Sn and Cu, is disclosed in U.S. Pat. No. 3,875,220. According to the working examples of this patent, the yield of methacrylic acid is not satisfactory, i.e., in the range of from 44.7% to 57.6%.

SUMMARY OF THE INVENTION

An object of the present invention is to provide a process for catalytically oxidizing methacrolein in the vapor phase to methacrylic acid wherein both the conversion of methacrolein and the selectivity to methacrylic acid are high and thus the yield of methacrylic acid is high even when the catalytic oxidation is carried out at a relatively low reaction temperature.

Another object of the present invention is to provide a catalyst exhibiting an enhanced catalytic activity for the oxidation of methacrolein to methacrylic acid and possessing an improved durability.

In accordance with the present invention, there is provided a process for the preparation of methacrylic acid by catalytically oxidizing methacrolein in the vapor phase with molecular oxygen at a temperature of from 200° C. to 450° C., characterized by using a catalyst consisting essentially of (A) molybdenum, (B) phosphorus, (C) potassium and/or cesium, (D) vanadium, (E) silver and/or tellurium and (F) oxygen and represented by the formula:

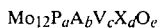

$$Mo_{12}P_aA_bV_cX_dO_e$$

wherein Mo is molybdenum, P is phosphorus, A is at least one metal selected from potassium and cesium, V is vanadium, X is at least one metal selected from silver and tellurium, and O is oxygen, and the subscripts a through d are positive numbers falling within the following ranges:

$a = 0.5$ to 5, preferably 0.9 to 3, $b = 0.1$ to 4, preferably 0.5 to 3, $c = 0.05$ to 3, preferably 0.1 to 2, and $d = 0.001$ to 2, preferably 0.01 to 1, and e is a positive number required by the valence states of the other elements present, the e being usually in the range of 39 to 60.

The advantages of the present invention over processes employing conventional molybdenum, phosphorus, potassium (and/or cesium) and vanadium-containing catalysts are summarized as follows. First, the conversion of methacrolein and the yield of methacrylic acid are enhanced to a considerable extent, i.e., approximately 10% or more, as will be apparent from the comparison of the Examples with Comparative Examples 1, 2 and 5, mentioned below. Secondly, a satisfactory yield of methacrylic acid is attainable even when the catalytic oxidation of methacrolein is carried out at a relatively low reaction temperature, e.g. from 300° to 340° C. and further even when the catalytic oxidation is continued over a long period of time.

DESCRIPTION OF THE PREFERRED EMBODIMENTS

The atomic ratios of the respective elements, expressed by the subscripts a through d in the above-mentioned formula are crucial for the intended advantages. For example, if the amount of the X ingredient, i.e., silver and/or tellurium, exceeds the above-mentioned range, the selectivity to methacrylic acid is reduced. In contrast, if the amount of the X ingredient is smaller than the above-mentioned range, the conversion of methacrolein is reduced.

It is thought that the respective elements (other than oxygen) present in the catalyst used are predominantly in the form of compounds of the type, in which two or more of the elements are bonded with oxygen, such as phosphomolybdic acid salts.

The catalyst used in the process of the invention may be prepared in any convenient manner by using, as the starting raw material, oxides, salts and other compounds, containing the respective elements. The general procedure for the preparation of the catalyst is as follows. Oxides, salts and other compounds, containing the respective elements, are mixed with each other in an aqueous medium to prepare a uniform solution or dispersion. The aqueous solution or dispersion is dried and then, calcined in an air atmosphere at a temperature of from 300° to 550° C., preferably from 350° to 450° C. for a period of from 2 to 24 hours, preferably from 3 to 15 hours.

The procedure for the preparation of the catalyst will be described in more detail in the following example. Predetermined amounts of a potassium salt and/or a cesium salt, e.g., potassium nitrate and/or cesium nitrate are combined with an aqueous solution of a molybdic acid salt, e.g., phosphomolybdic acid, while being stirred. Then, a predetermined amount of a vanadium salt, e.g., ammonium metavanadate, and predetermined amounts of a silver salt or oxide and/or a tellurium salt or oxide, e.g. silver nitrate and/or tellurium dioxide, are successively added to the above solution, while being stirred. The obtained aqueous slurry is evaporated to dryness, and then, the dried product is calcined at a temperature of from 300° to 550° C. for a period of from 2 to 24 hours. It should be understood, however, that the procedure by which the catalyst is prepared and the raw materials from which the catalyst is prepared are not limited to those described in this example, and other procedures and raw materials may be employed.

Illustrations of the starting raw materials for use in the preparation of the catalyst are enumerated, for example, ammonium molybdate, molybdic acid, phosphomolybdic acid, phosphoric acid, ammonium phosphate, potassium nitrate, cesium nitrate, potassium carbonate, cesium carbonate, potassium hydroxide, cesium hydroxide, potassium phosphate, metavanadic acid, ammonium metavanadate, vanadium pentoxide, silver nitrate, silver sulfate, silver chloride, silver carbonate, telluric acid, potassium tellurate, tellurium chloride and tellurium dioxide.

The catalyst may be used alone or in combination with a carrier. The use of a carrier is advantageous in enhancement of the mechanical strength of the catalyst. As carriers, those which are known for use in supporting conventional oxidation catalysts, such as diatomaceous earth, silica, alumina, silicon carbide, silica-alumina and water-soluble silica sol may be used.

In general, the size and shape of the catalyst particulates used are not particularly critical because they do not greatly effect the catalytic activity. Pellets, tablets and other optional shapes may be used depending upon the conditions under which the catalysts are used.

Molecular oxygen used in the catalytic oxidation of the invention is not necessarily highly purified; however, air or other oxygen-containing gases may also conveniently be used. Particularly, air may be advantageously used. The amount of molecular oxygen used is usually in the range of from 0.5 to 7 moles, more preferably from 1 to 5 moles, per mole of methacrolein.

Methacrolein used in the catalytic oxidation is also not necessarily highly purified, and its mixtures may be used. For example, a gaseous product obtained by the oxidation of isobutylene may be used. A gaseous product obtained by the oxidation of a hydrocarbon mixture containing n-butene and isobutylene, such as a spent BB which is a residue obtained by separating 1,3-butadiene from the $C_4$ fraction produced by the thermal cracking of naphtha, may also be used. However, a mixture containing salient amounts of unsaturated aldehydes other than methacrolein should not be employed because such a mixture not only retards the catalytic oxidation reaction involved but also produces polymer and other side-reaction products.

A gaseous feed comprising methacrolein and molecular oxygen may contain a diluent gas which does not influence the catalytic oxidation reaction involved. Such a diluent gas includes, for example, steam, nitrogen and carbon dioxide. Among others the incorporation of steam in the gaseous feed is preferable, because steam not only acts as a diluent but also exhibits effects for enhancing the selectivity to methacrolein and further makes the catalytic activity durable. The amount of steam incorporated in the gaseous feed is preferably in the range of from 1 to 30 moles, more preferably from 2 to 10 moles, per mole of methacrolein.

It is convenient to carry out the catalytic oxidation reaction under atmospheric pressure although superatmospheric or subatmospheric pressure may be employed if desired. The catalytic oxidation reaction may be carried out at a temperature in the range of from 200° C. to 450° C., preferably 250° to 400° C. The optimum reaction temperature is in the range of from 300° to 340° C. The contact time is usually in the range of from 0.1 to 10 seconds, preferably from 0.5 to 5 seconds.

The catalytic oxidation reaction may be carried out in a fixed bed, a moving bed or a fluidized bed. It is generally preferable to employ a fixed bed. This is because the catalyst used in the process of the invention not only exhibits a high catalytic activity for the oxidation reaction involved even when the oxidation reaction is carried out at a relatively low temperature, but also can maintain its activity over a long period of time.

The methacrylic acid produced may be recovered by any convenient manner, such as condensation or extraction with a solvent.

The present invention will be further clarified by the following examples and comparative examples, wherein conversion of methacrolein, selectivity to methacrylic acid and yield of methacrylic acid were calculated in accordance with the following equations.

% Conversion of methacrolein =
$$\frac{\text{moles of methacrolein consumed}}{\text{moles of methacrolein fed}} \times 100$$

% Selectivity to methacrylic acid =
$$\frac{\text{moles of methacrylic acid produced}}{\text{moles of methacrolein consumed}} \times 100$$

% Yield of methacrylic acid =
$$\frac{\text{moles of methacrylic acid produced}}{\text{moles of methacrylic fed}} \times 100$$

EXAMPLE 1

300 g of phosphomolybdic acid [$H_3PMo_{12}O_{40}.29H_2O$] were dissolved in one liter of water maintained at 80° C. A solution of 25.7 g of potassium nitrate [$KNO_3$] in 100 ml of water was added to the aqueous molybdic acid solution, while the mixture was being stirred. 7.45 g of ammonium metavanadate [$NH_4VO_3$] and 2.0 g of tellurium dioxide [$TeO_2$] were successively added to the mixed solution. The slurry so obtained was heated, while being stirred, to be thereby concentrated and thereafter, evaporated almost to dryness with a drum dryer. The product was maintained at 200° C. thereby being completely dried. The dried product was shaped into tablets 5 mm in diameter and 5 mm in height by using a tableting machine. The tablets were calcined at 400° C. for 5 hours in air to prepare a catalyst. The atomic ratio of the respective elements (other than oxygen) present in the catalyst was Mo:P:K:V:Te=12:1:2:0.5:0.1.

Ten ml of the catalyst were packed in a tubular glass reactor having an inner diameter of 8 mm. A gaseous mixture comprised of, by volume, 4% of methacrolein, 10% of molecular oxygen, 30% of steam and 56% of nitrogen was passed through the catalyst-packed reactor maintained at 330° C. at a flow rate of 150 ml/min. The contact time was 4.0 seconds. The catalytic oxidation was continued over a period of 5 hours. Results of the catalytic oxidation are shown in Table I, below.

EXAMPLES 2 THROUGH 14

Following a procedure similar to that mentioned in Example 1, catalysts having the compositions shown in Table I, below, were prepared. Besides the starting compounds used in Example 1, cesium nitrate [$CsNO_3$] and silver nitrate [$AgNO_3$] were used as cesium and silver sources, respectively.

Using these catalysts separately, the catalytic oxidation of methacrolein was carried out under conditions similar to those mentioned in Example 1, wherein the reaction temperature was set, as shown in Table I, below. Results of the catalytic oxidation are shown in Table I, below.

TABLE I

| Example No. | Catalyst composition (exclusive of oxygen; atomic ratio) | | | | | | | Reaction temperature (°C.) | Conversion of methacrolein (%) | Selectivity to methacrylic acid (%) | Yield of methacrylic acid (%) |
|---|---|---|---|---|---|---|---|---|---|---|---|
| | Mo | P | K | Cs | V | Ag | Te | | | | |
| 1  | 12 | 1   | 2   | —   | 0.5  | —   | 0.1  | 330 | 97.3 | 75.8 | 73.8 |
| 2  | 12 | 1   | 2   | —   | 0.5  | 0.1 | —    | 330 | 95.4 | 77.3 | 73.7 |
| 3  | 12 | 1   | 2   | 0.2 | 1    | —   | 0.1  | 330 | 94.0 | 78.6 | 73.9 |
| 4  | 12 | 1   | 2   | 0.1 | 1    | 0.2 | 0.2  | 320 | 96.8 | 79.4 | 76.9 |
| 5  | 12 | 1.5 | 1.5 | 0.5 | 0.5  | 0.1 | —    | 330 | 93.9 | 80.1 | 75.2 |
| 6  | 12 | 0.9 | 1.8 | —   | 0.4  | —   | 0.4  | 330 | 97.6 | 76.8 | 75.0 |
| 7  | 12 | 1.1 | 1.6 | 1.1 | 0.6  | —   | 0.1  | 320 | 95.2 | 78.9 | 75.1 |
| 8  | 12 | 1   | 2   | —   | 0.5  | 0.1 | 0.1  | 320 | 94.7 | 76.8 | 72.8 |
| 9  | 12 | 1   | 2   | —   | 0.5  | 0.5 | —    | 330 | 95.0 | 76.1 | 72.3 |
| 10 | 12 | 1   | 2   | 0.3 | 0.4  | —   | 0.01 | 330 | 98.0 | 80.1 | 78.5 |
| 11 | 12 | 1   | —   | 2   | 0.5  | —   | 0.1  | 330 | 98.2 | 74.0 | 73.6 |
| 12 | 12 | 2   | 2   | —   | 0.5  | 0.1 | —    | 330 | 94.8 | 80.3 | 76.1 |
| 13 | 12 | 1   | 1   | —   | 0.1  | 0.1 | —    | 330 | 98.6 | 72.8 | 71.9 |
| 14 | 12 | 2   | 2   | —   | 0.75 | —   | 0.01 | 330 | 94.8 | 76.7 | 72.8 |

Contact time: 4.0 seconds

COMPARATIVE EXAMPLES 1 THROUGH 5

Following a procedure similar to that mentioned in Example 1, catalysts having the compositions shown in Table II, below, were prepared which compositions were outside the range claimed in the present application.

Using these catalysts separately, the catalytic oxidation of methacrolein was carried out under conditions similar to those mentioned in Example 1, wherein the reaction temperature was set as shown in Table II, below. Results of the catalytic oxidation are shown in Table II, below.

TABLE II

| Comparative Example No. | Catalyst composition (exclusive of oxygen; atomic ratio) | | | | | | | Reaction Temperature (°C.) | Conversion of methacrolein (%) | Selectivity of methacrylic acid (%) | Yield of methacrylic acid (%) |
|---|---|---|---|---|---|---|---|---|---|---|---|
| | Mo | P | K | Cs | V | Ag | Te | | | | |
| 1 | 12 | 1 | 2 | —   | 0.5 | —   | —   | 340 | 85.4 | 74.8 | 63.9 |
| 2 | 12 | 1 | 2 | 0.2 | 1   | —   | —   | 340 | 82.6 | 76.7 | 63.4 |
| 3 | 12 | 1 | 2 | —   | —   | 0.1 | —   | 330 | 82.3 | 64.1 | 52.8 |
| 4 | 12 | 1 | 2 | —   | —   | —   | 0.1 | 330 | 85.1 | 60.3 | 51.3 |
| 5 | 12 | 2 | — | 2   | 1.5 | —   | —   | 330 | 70.4 | 75.3 | 53.0 |

Contact time: 4.0 seconds

COMPARATIVE EXAMPLES 6 AND 7

Following a procedure similar to that mentioned in Example 1, two catalysts were prepared wherein niobium pentoxide [$Nb_2O_5$] (in Comparative Example 6) and tantalum pentoxide [$Ta_2O_5$] (in Comparative Example 7) were separately used instead of ammonium metavanadate. The two catalysts contained the respective ingredients at the atomic ratios shown in Table III, below.

Using the two catalysts separately, the catalytic oxidation of methacrolein was carred out under conditions similar to those mentioned in Example 1. Results are shown in Table III, below.

TABLE III

| Comparative Example No. | Catalyst composition (exclusive of oxygen; atomic ratio) | | | | | | Reaction temperature (°C.) | Conversion of methacrolein (%) | Selectivity to methacrylic acid (%) | Yield of methacrylic acid (%) |
| --- | --- | --- | --- | --- | --- | --- | --- | --- | --- | --- |
| | Mo | P | K | Nb | Ta | Te | | | | |
| 6 | 12 | 1 | 2 | 1 | — | 0.1 | 330 | 89.3 | 60.3 | 53.8 |
| 7 | 12 | 1 | 2 | — | 1 | 0.1 | 330 | 98.1 | 58.1 | 57.0 |

Contact time: 4.0 seconds

EXAMPLE 15

Using a catalyst similar to that prepared in Example 1 and having the composition of $Mo_{12}P_1K_2V_{0.5}Te_{0.1}$, the catalytic oxidation of methacrolein was carried out continuously over a period of 1,000 hours. After the 1,000 hours' operation, no deterioration of the catalyst was observed, and the conversion of methacrolein, the selectivity to methacrylic acid and the yield of methacrylic acid were 97.0%, 76.2% and 73.9%, respectively.

What we claim is:

1. An improvement in the process for the preparation of methacrylic acid by catalytically oxidizing methacrolein in the vapor phase with molecular oxygen at a temperature of from 200° C. to 450° C., said improvement comprising using a catalyst consisting essentially of (A) molybdenum, (B) phosphorus, (C) potassium and/or cesium, (D) vanadium, (E) silver and/or tellurium and (F) oxygen and represented by the formula:

$$Mo_{12}P_aA_bV_cX_dO_e$$

wherein Mo is molybdenum, P is phosphorus, A is at least one metal selected from potassium and cesium, V is vanadium, X is at least one metal selected from silver and tellurium, and O is oxygen, and the subscripts a through d are positive numbers falling within the following ranges: a=0.5 to 5, b=0.1 to 4, c=0.05 to 3 and d=0.001 to 2, and e is a positive number required by the valence states of the other elements present.

2. A process according to claim 1 wherein said catalyst is the calcined residue obtained by calcining at a temperature of from 300° to 550° C. a product formed by mixing the respective element-containing compounds in an aqueous medium and then drying the mixture.

3. A process according to claim 2 wherein said calcined residue is obtained by calcining said mixing and dried product at a temperature of from 350° to 450° C. for a period of from 2 to 24 hours in an air atmosphere.

4. A process according to claim 1 or 2 wherein the atomic ratios of the respective elements to molybdenum are such that the subscripts a through d are positive numbers falling within the following ranges: a=0.9 to 3, b=0.5 to 3 c=0.1 to 2 and d=0.01 to 1.

5. A process according to claim 1 or 2 wherein X in the formula is silver.

6. A process according to claim 1 or 2 wherein X in the formula is tellurium.

7. A process according to claim 1 or 2 wherein X in the formula is silver plus tellurium.

8. A process according to claim 1 or 2 wherein the catalytic oxidation of methacrolein is effected at a temperature of from 250° to 400° C. with a contact time of from 0.1 to 10 seconds.

9. A process according to claim 1 or 2 wherein the catalytic oxidation of methacrolein is effected at a temperature of from 300° to 340° C. with a contact time of from 0.5 to 5 seconds.

10. A process according to claim 1 or 2 wherein the amount of molecular oxygen is in the range of from 0.5 to 7 moles per mole of methacrolein.

11. A process according to claim 1 or 2 wherein the catalytic oxidation of methacrolein is effected in the presence of 1 to 30 moles of steam per mole of methacrolein.

* * * * *